United States Patent [19]

Grunwald et al.

[11] Patent Number: 4,804,359
[45] Date of Patent: Feb. 14, 1989

[54] CARDIOVASCULAR CANNULA AND OBTURATOR

[75] Inventors: Ronald P. Grunwald, Valleyford, Wash.; Robert J. Todd, Salt Lake City, Utah

[73] Assignee: Research Medical, Inc., Salt Lake City, Utah

[21] Appl. No.: 112,723

[22] Filed: Oct. 23, 1987

[51] Int. Cl.$^4$ .................. A61M 5/00; A61M 25/00
[52] U.S. Cl. .................................. 604/4; 604/27; 604/284
[58] Field of Search ..................... 604/4, 27, 284, 280

[56] References Cited

U.S. PATENT DOCUMENTS

| | | | |
|---|---|---|---|
| 945,741 | 1/1910 | Birkenkamp | 128/343 |
| 2,587,910 | 3/1952 | Shulman | 604/284 X |
| 2,624,341 | 1/1953 | Wallace | 128/350 |
| 2,935,068 | 5/1960 | Donaldson | 128/348 |
| 3,460,541 | 8/1969 | Doherty | 128/351 |
| 3,835,863 | 9/1974 | Goldberg et al. | 128/350 R |
| 3,903,895 | 9/1975 | Alley et al. | 128/350 R |
| 4,072,153 | 2/1978 | Swartz | 128/350 R |
| 4,114,618 | 9/1978 | Vargas | 128/214.4 |
| 4,129,129 | 12/1978 | Amrine | 128/214 R |
| 4,142,528 | 3/1979 | Whelan, Jr. et al. | 128/350 R |
| 4,248,224 | 2/1981 | Jones | 128/214 R |
| 4,309,994 | 1/1982 | Grunwald | 128/214 R |

Primary Examiner—Dalton L. Truluck
Attorney, Agent, or Firm—Wells, St. John & Roberts

[57] ABSTRACT

An improved venous cannula and obturator for interconnecting the superior and the inferior vena cava to the venous return line of a heart-lung machine. The cannula includes a pair of resilient, divergent hollow branches. The branches are of unequal length. The longer branch is to be received within the inferior vena cava and the shorter branch is to be received in the superior vena cava. The open branch ends are thus longitudinally staggered when the branches are clamped together by the obturator to facilitate insertion of the branch ends through a single incision within the atrium and ultimate disposition of the branches in the superior and inferior vena cavae. The obturator includes an elongated rod with a hub having a pair of axial legs to be received within the branches of the cannula. The obturator is provided to be slidably received with minimal frictional resistance within the interior lumen of the cannula and the cannula branches. The obturator includes features to minimize frictional resistance to axial movement of the obturator in the cannula, and that facilitate release of the cannula branches to separate within the atrium.

22 Claims, 5 Drawing Sheets

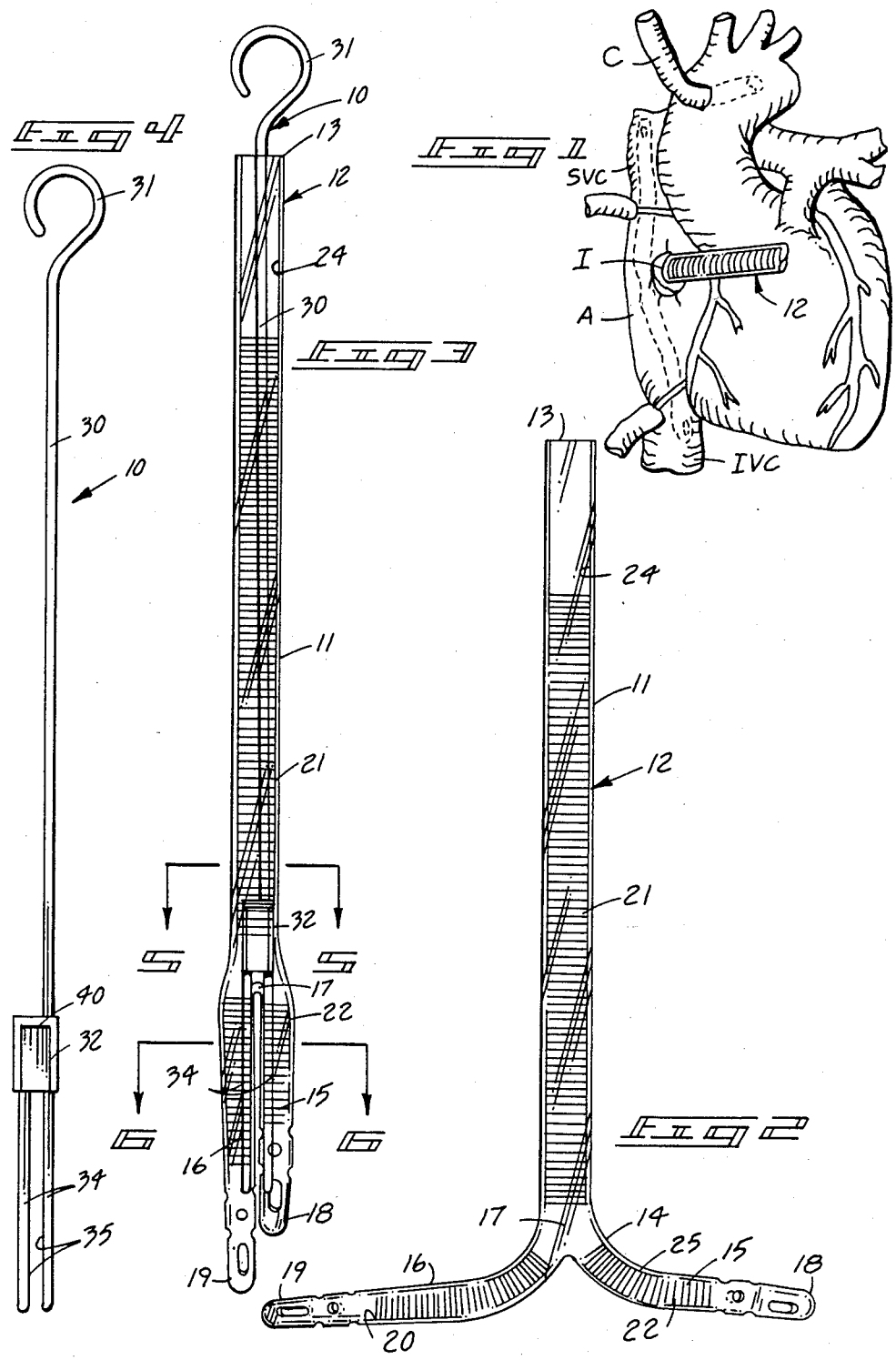

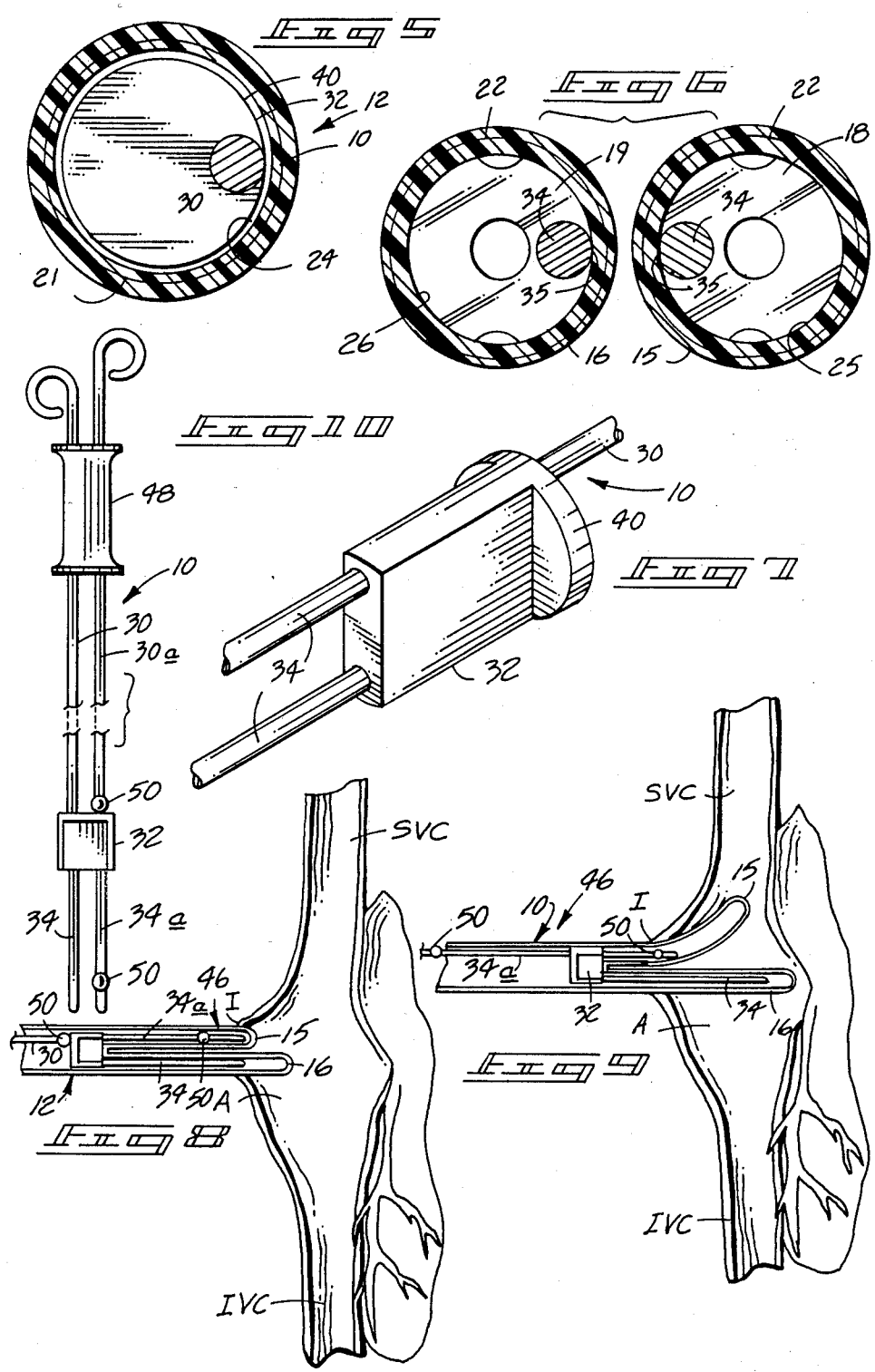

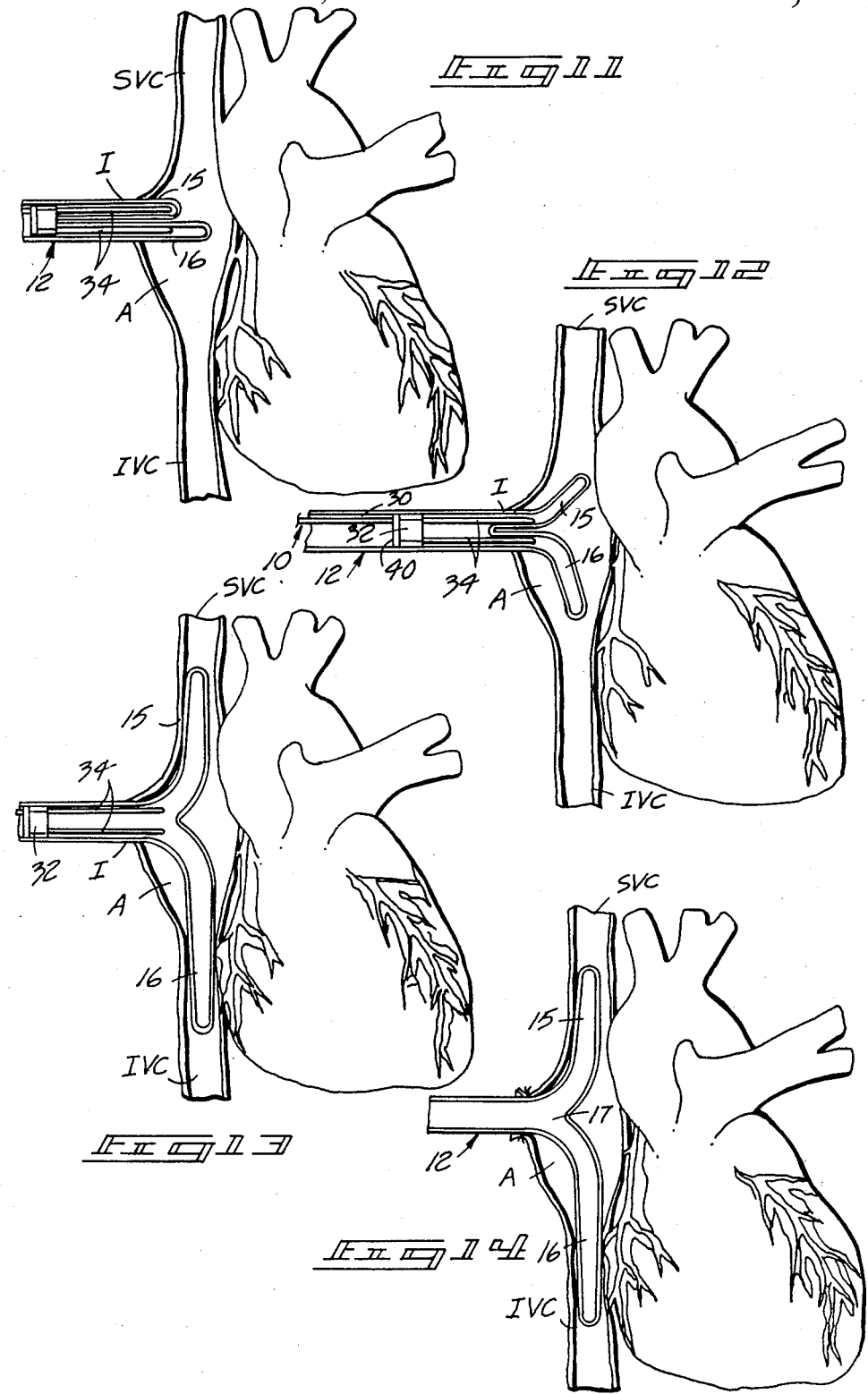

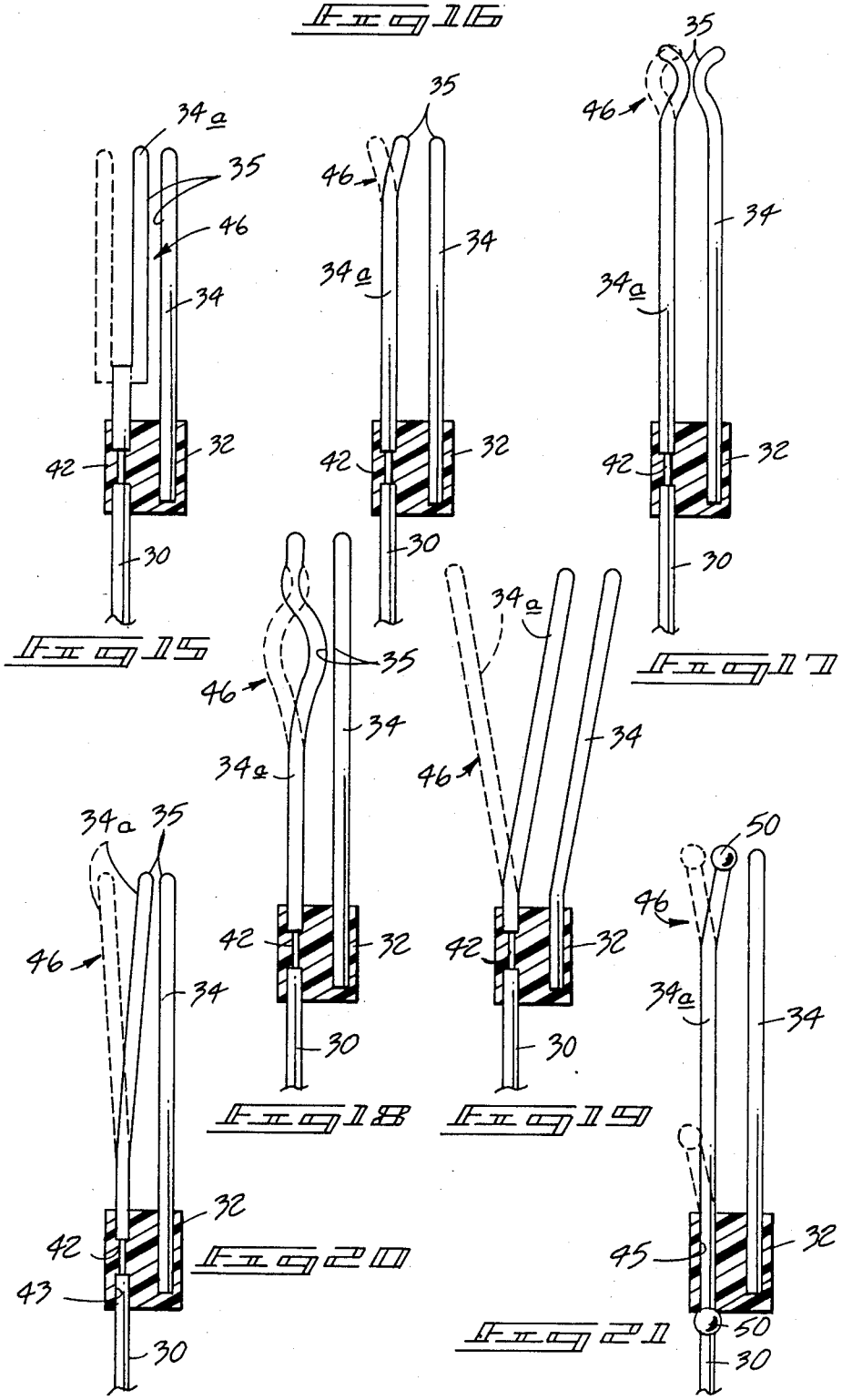

CARDIOVASCULAR CANNULA AND OBTURATOR

TECHNICAL FIELD

The present invention relates generally to cannulation of the superior and inferior vena cavae and more particularly to cannulation of the superior and inferior vena cavae using a single bifurcated cannula.

BACKGROUND OF THE INVENTION

In prior surgical techniques wherein the patient's blood circulation system is diverted through an extracorporeal heart-lung circuit, it has been common to use a pair of venous return cannulas inserted in the neighborhood of the appendix of the right atrium of the heart. The auricular appendix is convenient for clamping purposes and is also conveniently located for cannulation. However, double cannulation is not easily accomplished through the appendix of the atrium, since there is insufficient space to insert the two cannula tubes.

The double incisions required for the above form of cannulation technique requires placement of two separate snare sutures for the cannulas surrounding the two individual incisions. This takes preparation time and increases the trauma to the area due to the two separate incisions. Furthermore, the two cannulas, once inserted, often obstruct the area and further delay the surgical process.

In the typical two cannula arrangement, a third cannula is used for infusion of blood from the heart-lung machine. This cannula is typically inserted into the aorta. The two drainage tubes and the infusion tube often hinder positioning of the heart to facilitate aortocoronary bypasses, valve implants, etc. In addition, the several tubes hinder direct access by the various surgical instruments used in such operations.

It becomes desirable, since the venous drainage cannulas lead to the same phlebotomy line of the extracorporeal circuit to use a single cannula inserted through a single incision in the atrial appendix.

U.S. Pat. No. 4,309,994 to Grunwald, co-inventor in this application, discloses a bifurcated cannula and internal obturator that are now in common use as a solution to the double cannulation problems indicated above. The cannula includes resilient branches at an inward end, one that is receivable within the superior vena cava and the other for descending the inferior vena cava. Both branches diverge from the central axis of a single tube. An obturator having a cross-sectional configuration matching the cross-sectional shape of the cannula is slidably received within the tube. The obturator includes relatively straight bifurcated legs that are used to hold the cannula branches together along the tube axis during initial insertion. The obturator legs also enable the cannula branch ends to separate within the atrium following initial insertion. the obturator is shaped along its full length to slidably engage the internal configuration of the cannula and branches to hold the cannula straight with the branches together to facilitate insertion of the cannula into the atrium and to prevent reflux of blood through the cannula by close frictional engagement of the obturator along the cannula. While this assembly has operated effectively, some difficulty has been experienced in insertion of the cannula and separation of the branches due to frictional resistance to axial movement of the obturator within the cannula.

U.S. Pat. No. 4,248,224 to Jones discloses a double venous cannula that makes use of a bifurcated cannula tube having an external obturator in the form of a second tubular member. The external obturator is received axially over the length of the primary cannula tube and includes an end that is used to cam the bifurcated cannula branches together and apart to facilitate insertion and removal of the cannula branches into the superior and inferior vena cavae. The cannula branches in this version extend from a crotch of the tube that remains exposed outwardly of the incision site. The incision is closed by purse sutures about the two separate branches of the cannula. The tissues engaged about the two individual branches may not be adequately gathered about the two tubes, especially in areas adjacent to the tangential points of contact of the two tubes. Interstices are therefore formed between the tubes and the adjacent tissues at the incision site. Unless these areas are otherwise plugged, the interstices will permit reflux of blood.

A double cannula arrangement is shown in U.S. Pat. No. 3,903,895 to R. D. Alley, et al. This patent shows a venous return line of an extracorporeal circuit with a double tubular end, one cannula end being inserted through an incision in the atrium and extending upwardly into the superior vena cava, while the remaining cannula is inserted through a second incision to descend into the inferior vena cava. The two branches extend outwardly of the heart to connect with converging lines to the heart-lung circuit.

U.S. Pat. No. 3,835,863 to Goldberg discloses a "T" tube that is used as a drainage catheter for implantation in an internal duct. Transverse arms of the "T" tube are slotted longitudinally to enable folding over one another to the diameter of the main tube branch. The tubes can thus be folded onto one another and inserted through an incision in the associated duct. Upon insertion, the two branches may spring apart, opening into the duct. Withdrawal of the tube is accomplished simply by pulling the tube outwardly. The transverse branches of the tube will fold together at the incision as the tube is pulled outwardly.

The Goldberg "T" tube may have beneficial use in the drainage of internal ducts such as bile ducts in abdominal surgery. However, such a drainage tube would not be functional for use as a venous return cannula due to the open slots formed along the two branches. Furthermore, the open tubes would not lend themselves easily to operation with an obturator by which the branch ends would be guided upon insertion or withdrawal through a single incision.

The preferred embodiments disclosed herein provide distinctive improvements that are not shown or suggested by the known prior art. The disclosed cannula and obturator include provisions that significantly ease insertion of the cannula and that facilitate placement of the cannula branches within the superior and inferior vena cavae with minimal manipulation.

BRIEF DESCRIPTION OF THE DRAWINGS

Preferred embodiments of the invention are illustrated in the accompanying drawings, in which:

FIG. 1 is a diagrammatic view illustrating a heart with a bifurcated cannula in its operative position;

FIG. 2 is an elevation view of the cannula;

FIG. 3 is a view of the cannula and an obturator assembly with the branches of the cannula being drawn together by legs of the obturator;

FIG. 4 is a view of an exemplary obturator;

FIG. 5 is an enlarged sectional view taken substantially along line 5—5 in FIG. 3;

FIG. 6 is an enlarged sectional view taken substantially along line 6—6 in FIG. 3;

FIG. 7 is an enlarged view of an obturator hub with the obturator rod and legs broken away;

FIGS. 8 and 9 are operational diagrams illustrating initial steps of insertion of the cannula and a sliding leg type obturator;

FIG. 10 is a view of a double rod and leg obturator;

FIG. 11 through 14 are progressive operational diagrams illustrating insertion of the cannula using the obturator form shown in FIG. 4;

FIGS. 15 through 21 illustrate various obturator leg configurations; and

DETAILED DESCRIPTION OF THE PREFERRED EMBODIMENTS

Figure 22:
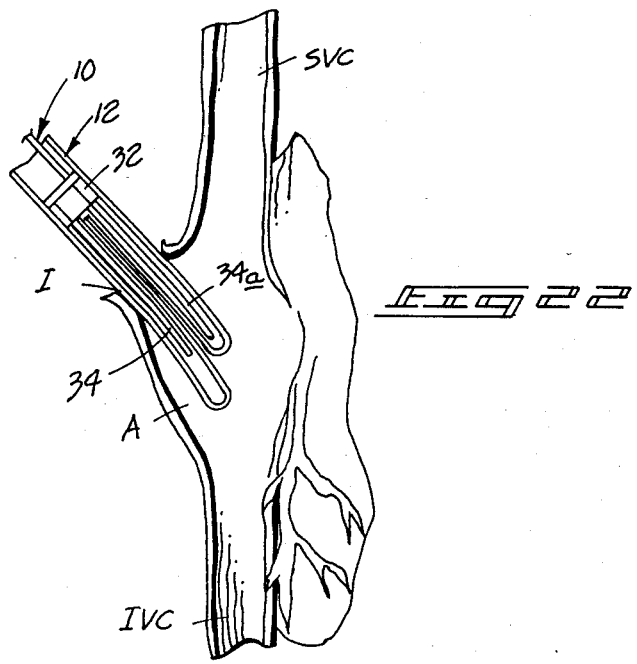
FIGS. 22 through 24 illustrate operation of a curved branch obturator and its use for inserting a cannula.

The following disclosure of the invention is submitted in compliance with the constitutional purpose of the Patent Laws "to promote the progress of science and useful arts" (Article 1, Section 8).

The present invention is exemplified by a cannula assembly including a cannula 12 and an obturator 10.

The cannula assembly, including the cannula 12 and obturator 10, are intended for use in cannulation of the right atrium (A), connecting blood flow from the superior vena cava (SVC) and the inferior vena cava (IVC) to the phlebotomy line of a conventional extracorporeal heart-lung system (not shown) for cardiovascular bypass. Use of the cannula 12 in accomplishing this function is illustrated diagrammatically by FIG. 1 of the drawings. The cannula is there shown extending through a single incision (I) in the appendix of the right atrium with bifurcated branches of the cannula extending respectively up the SVC and down the IVC. FIG. 1 also illustrates an infusion cannula (C) (not a component of the present invention) inserted into the aorta.

The cannula 12 includes an elongated hollow body 11 having an open outward end 13 with a central axial lumen 24 leading from end 13 to a bifurcated inward end 14 forming a "T" configuration. The bifurcated end 14 is characterized by a pair of branches 15, 16 that lead from a crotch 17 of the body 11 to blunt apertured tips 18, 19, respectively, at free open tube ends. The apertured tips are shown in detail by FIGS. 2 and 3 and substantially diagrammatically in the remaining Figures.

The central lumen 24 opens at the outward end 13 for connection to a phlebotomy line. The lumen 24 is formed by an internal tube wall along a central longitudinal axis of the tube body 11 and leads into integral smaller bore lumen 25, 26, formed through the respective branches 15, 16.

A preferred external diametric measurement of the main branch is 51 French (one French equaling 0.0131 inches). It is preferred that the two branches 15, 16 include exterior diametric dimensions totaling between approximately 51-72 French. The above dimensions are given for a range of branch sizes, with smaller sizes being used for small children and larger sizes for adults. A cannula with the above dimensions facilitates superior drainage capability over a standard venous cannula while minimizing the incision length required for insertion.

The cannula may be produced with internal branch lumen of different diameters. For example, the SVC branch 15 is advantageously 32 French while the IVC branch measures 36 French for average size adult patients. A smaller version may include an IVC branch 16 measuring 32 French and a SVC branch 15 measuring 28 French. A large size might include a 32 French for the SVC branch 15 and a 40 French for the IVC branch 16.

The cannula branch size is related to the relative amount of blood flow through the IVC and SVC. Approximately 70 percent of the total flow through the two cavae flows through the IVC while 30 percent flows through the SVC.

Another important feature of the cannula is noted in FIG. 3. The SVC branch 15 is shorter than the IVC branch 16. It is advantageous that the shorter SVC branch 15 be approximately one inch less in length than the longer IVC branch 16. This results in a staggered longitudinal relationship of the branch ends (FIG. 3) when the branches are brought together for insertion through the single incision. Upon insertion, the longer branch will progressively dilate the incision site for acceptance of the shorter branch end.

It is also desirable to utilize varying length cannula branches 15, 16 due to the nature of the SVC and IVC. The IVC is capable of receiving a cannula of substantial length since there are no significant venous branches within the IVC directly adjacent to the heart. The SVC, on the other hand, includes venous branches that are in relatively close proximity to the heart. It is therefore advantageous that the shorter cannula branch 15 be utilized for insertion within the SVC with its open end situated below any significant venous branches thereof and that the longer cannula branch 16 be situated within the IVC. Actual length of the SVC and IVC cannula branches may vary with the size of the patient. Small patients may utilize a cannula having 2¾ and 3⅜ inch branch length, medium size patients may utilize a cannula having 3½ and 4½ inch branch lengths, while larger patients may utilize a cannula having 4½ and 5½ inch branch lengths.

The cannula branches are resilient, normally diverging from the main cannula body to form a "Y" configuration (inverted in FIG. 2). To facilitate this feature, a preferred material for forming the cannula is dip mold plastisol formed of finely ground polyvinyl chloride mixed in a suspension with a plasticizing agent. Such material is acceptable for surgical use and includes a "memory" to facilitate resilient, normal separation of the cannula branches 15, 16, to their normally diverging configuration. This resilient material also enables manipulation of the branches to the closed configuration as shown by example in FIG. 3 to permit insertion and retraction of the cannula through a single incision. Other materials known to those skilled in the art, for example, polyurethanes or silicone, elastomers and others, either singly or in combination may also be utilized.

The cannula 12 may include a reinforcing spring 21 along its main tubular body 11. It may also include similar reinforcing springs 22 along the branches 15, 16. These springs may be embedded within the resilient cannula material to enhance resiliency of the material and to prevent the associated lumen 24, 25, 26 from collapsing or crimping when in use.

FIG. 4 illustrates a first preferred form of the present improved obturator 10. Other preferred forms of the present obturator are shown in FIGS. 10 through 24. All the various obturator forms shown include similar important features. Similar features for each of the obturators shown in the drawings will therefore be referred to collectively, and by the same reference numerals.

Obturator 10 includes an elongated rod 30 extending along an axis from a top handle end 31 to a hub 32. The hub 32 mounts a pair of axial obturator legs 34, projecting from the hub opposite to the rod 30. It is advantageous that one of the legs 34 be integral with the rod 30.

Means is provided along the obturator 10 for minimizing frictional resistance to movement of the rod 30 and legs 34 within the cannula. To this end, it is significant to note the cross-sectional dimensions of the rod 30 and legs 34, in comparison to the cannula lumen 24–26. As may be noted in FIG. 6, the cross-sectional dimension of each leg 34 is substantially less than the similar cross-sectional dimension of the adjacent branch lumen 25, 26. It may also be noted in FIG. 5 that the cross-sectional dimension of the rod 30 is substantially less than that of the central cannula lumen 24. The reduced leg and rod cross-sectional dimensions thus facilitate substantially free, low friction movement of the obturator axially within the cannula.

To further facilitate minimal frictional resistance to axial movement, the obturator legs include facing curved gripping surfaces 35 that tangentially contact wall surfaces of the branch lumen 25, 26 as shown in FIG. 6. The legs 34 will effectively hold the branches together, but their gripping surfaces 35 will slide relatively freely in axial directions to facilitate axial insertion and removal of the obturator into and out from the cannula and the cannula branches.

The small diameter obturator rod and legs may be formed of a substantially rigid material such as stainless steel having sufficient stiffness even in the small cross-sectional dimensions shown to selectively spring the cannula branches to a closed position for insertion as shown in FIG. 3. Other materials including reinforced thermoplastic may be substitued by those skilled in the art.

The small diameter rod 30 and legs 34 will permit relatively free passage of blood within the cannula. Blood reflux through the cannula, however, is minimized through provision of the hub 32. It may be formed to include an annular wiping edge 40 (FIG. 7) that is just slightly smaller in cross-sectional dimension than the cross-sectional dimension of the main lumen 24 (see FIG. 5). The edge 40 slidably obstructs the main lumen 24 of the cannula to prevent reflux of blood beyond the hub 32 upon insertion of the cannula. The axial extent of the edge 40 is insufficient to produce significant frictional drag against the walls of the central lumen as the obturator is moved therein.

The hub 32 may be formed of injection molded plastic, formed about rod 30 and legs 34. The rod 30 and one or both of the legs 34 may be permanently anchored by the hub 32. For example, in the obturator shown in FIGS. 3 and 4, and partially in the operative positions shown in FIGS. 11–13, the hub 32 mounts both legs 34 in a parallel stationary relation. In other obturator versions shown and described below, the hub 32 may include a release means 46, augmenting the means for reducing frictional resistance by enabling selective movement of one obturator leg relative to the other.

The release means 46 is provided for selectively moving one of the obturator legs 34a relative to the other leg 34 between a release position wherein the obturator legs are spaced apart by first distance and a gripping position wherein at least portions of the obturator legs are spaced apart by a second distance that is less than the first distance. Several examples of the release means 46 are shown in FIGS. 8, 9 and 15–21 where the first and second distances are indicated by respective dashed and solid lines. In these versions it is preferred that one of the legs 34a be integral with the rod 30 so that movement of the rod 30 will cause corresponding movement of the attached leg 34a.

The release means 46 includes features of the hub and at least the obturator leg 34a that facilitates motion of the one leg 34a relative to the other leg 34. As an example, a bore 43 is formed in the hub that will permit rotation of leg 34a relative to the other. An annular recess 42 (FIGS. 15–19) may be provided about the joined rod 30 and leg 34a within the hub. The recess 42 receives a complementary shaped portion 42a of the hub to allow rotation of the rod and leg yet prevent relative axial movement of the hub and rod-leg unit.

Figure 23:
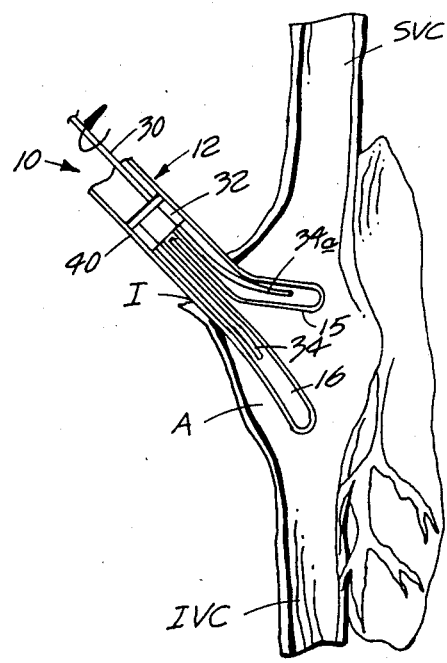

The rotatable leg 34a preferably includes a bend or angled section along its length, examples of which are shown in FIGS. 15 through 24 as a part of the release means 46. The bends will radially space the associated gripping surfaces 35 from the axis of the hub bore 43 so that the surfaces 35 will move between open release positions (dashed lines) and closed gripping positions (solid lines). The rods 30 may thus be rotated to selectively move the legs 34a and their gripping surfaces 35 to gripping positions (solid lines) to securely grip the cannula branches together as shown in FIG. 3, and to release positions (dashed lines) where the cannula branches are allowed to initially separate as indicated in FIG. 23.

Another example of the release means 46 is shown in a sliding leg obturator version by FIGS. 8, 9 and 21. Here, the hub 32 includes a relatively smooth open bore 45 (FIG. 21) extending through the hub to facilitate both axial motion and rotation of the rod and obturator leg 34a relative to the other leg 34. Beads 50 or other appropriate abutments may be positioned along the length of the movable leg 34a to act as stops, preventing axial movement of the leg beyond fully extended and retracted positions.

Axial separation of the leg ends in the sliding leg obturator is shown in FIGS. 8 and 9. FIG. 8 shows the obturator legs in a gripping position with their ends closely adjacent one another to clamp corresponding branches of the cannula closely together for insertion into the atrium. The sliding obturator leg 34a may also be moved axially outward, to the position shown in FIG. 9 where the leg ends are spaced apart axially in a "release" condition to allow separation of the cannula branches within the atrium.

With the above axially movable "slidable" leg obturator, separation of the legs between the first (FIG. 9) and second (FIG. 8) distances occurs axially as opposed to substantial radial or lateral separation of the leg ends with the rotatable obturator leg versions.

A combination of both movable obturator leg release features (rotatable and axially movable obturator legs) may be available in the example indicated in FIG. 21. There the obturator leg 34a is capable of both axial motion and rotational motion in relation to the remaining obturator leg 34. The gripping surface 35 of leg 34a is radially spaced from the axis of rotation for the rod (as defined by the hub bore) so rotation of the rod will result in rotation of its gripping surface 35 in a circular path toward or away from the remaining leg 34. The hub bore will also allow the rod 30 to slide, axially moving the leg 34a between axially extended and retracted positions.

A double obturator rod is exemplified in FIG. 10 which may incorporate features of the release means including the axial sliding obturator leg features and rotatable leg features along with a double rod and handle to permit maximum manipulation of the cannula branches by use of the obturator. One of the rods 30a and its associated obturator leg 34 may be axially affixed to a hub 32 but may remain free to rotate, while the remaining rod 30 and leg 34a will both axially slide and freely rotate within the hub. Both obturator legs 34, 34a can thus be selectively moved axially or rotated, or both by manipulation of their handle ends.

A handle 48 may be provided for slidably guiding the outward ends of the two rods and providing a hand hold against which the individual rods can be actuated.

OPERATION

Operation of the cannula and obturator combination shown in FIGS. 3 and 4 is shown diagrammatically by FIGS. 11 through 14. The obturator and cannula are initially assembled as shown in FIG. 3 with the obturator extended fully into the cannula and with the obturator legs 34 received within the branches of the cannula. The curved gripping surfaces 35 of the relatively straight fixed obturator legs 34 slide axially along the length of the cannula branches camming the cannula branches together, and firmly clamping them in the closed position shown in FIG. 3 for insertion into the atrium. The relatively small areas of tangential contact between the obturator leg surfaces 35 and the contacted branch lumen surfaces facilitates relatively free, low friction axial motion of the obturator relative to the cannula.

The assembled cannula branches and obturator legs may be initially inserted through a single incision formed through the appendix of the right atrium as shown in FIG. 11. Insertion is facilitated by the staggered length cannula branches. The tip 19 of the longer branch 16 first enters through the incision, dilating the incision and facilitating reception of the tip 18 of the second, shorter cannula branch 15. Insertion of the cannula to the extent illustrated in FIG. 11 is therefore accomplished in a smooth and nearly effortless manner.

Insertion of the cannula may continue with the obturator being held stationary with the leg ends situated just inside the atrium (FIGS. 12 and 13). The resilient branches progressively spread as they slide from contact with the gripping surface 35 of the obturator legs.

It is pointed out that axial movement of the cannula in relation to the obturator is accomplished with relatively little frictional resistance between the two components. The surgeon can hold the obturator stationary while pushing the cannula inwardly, or slightly retract the obturator while simultaneously pushing inwardly on the cannula. In either manner, the cannula will slide inward with little frictional resistance and the branches 15, 16 will separate axially from the obturator leg ends and diverge within the atrium.

Insertion is made with the branches oriented such that the shorter cannula branch 15 bends upwardly to be received in the SVC and the lower, longer branch 16 is received downwardly within the IVC.

Blood reflux is prevented in the above steps by the wiping edge 40 along the hub 32. The wiping edge 40, and rounded surfaces 35 of the obturator legs are substantially the only surfaces that need be in frictional engagement with the cannula lumen, so resistance to motion within the cannula is held at a minimum. Such minimal contact permits low friction, axial motion of the obturator within the cannula, without hesitant, jerky motions that could adversely influence guidance and reception of the cannula branches within the respective SVC and IVC.

Once the cannula branches fully separate due to their natural resiliency and are received within the SVC and IVC, and when the crotch of the cannula is situated well within the atrium, the obturator may be fully removed from the cannula. Purse string sutures may then be tightened about the cannula and appropriate connections may be made with the extracorporeal heart-lung machine. If desired, appropriate tapes (FIG. 1) may be used to secure the tips of the cannula branches within the vena cavae.

Removal of the cannula may simply involve insertion of the obturator through the outward cannula end to bring the obturator legs into the atrium. The obturator is then held axially stationary in this position as the cannula is withdrawn. The legs of the obturator will cam the cannula branches together just inside the incision site to avoid stretching or tearing of the tissues at the incision site as the cannula branches are withdrawn. The hub 32 and its wiping edge 40 act to minimize withdrawal of blood along with the cannula branches as the cannula is withdrawn. Complete withdrawal may follow as the cannula is drawn fully over the obturator and the otherwise divergent branches are again progressively clamped by the obturator legs as the cannula is retracted. The cannula branches may then be fully withdrawn from the atrium so the incision may be closed.

Operation of the sliding leg obturator and cannula may be understood with reference to FIGS. 8 and 9. Insertion of the obturator into the cannula is made in basically the same manner as described above, with the rod 30 being axially received along the full length of the cannula and with both obturator legs 34, 34a being received within respective cannula branches. The obturator leg surfaces 35 cam against the cannula branches, drawing them together for insertion through the single incision in the atrium. Bead 50 prevents leg 34a from sliding too far forward during insertion.

Insertion of the cannula branch ends is shown in FIG. 8 where the longer branch 16 of the cannula has been inserted into the atrium, followed by the shorter branch 15. The staggered branch lengths facilitate insertion by progressively dilating the incision as noted above.

Once both cannula branches are inserted partially within the atrium, the obturator rod 30 may be held stationary with the end bead 50 in the vicinity of the incision site as insertion of the cannula and the remaining branch 34 continue. This action allows the cannula branch 15 to resiliently diverge at least partially toward its normal outward orientation as indicated in FIG. 9. The slidable obturator leg 34a will ultimately withdraw (with respect to the other leg 34) only to the point where the bead 50 on the obturator leg 34a engages the hub 32. Further pull along the obturator rod 30 or inward thrust of the cannula will cause the remaining obturator leg 34 to retract axially from the cannula, withdrawing from the remaining cannula branch 16. That branch will then begin its outward migration, seeking out the adjacent IVC.

It is pointed out that the example illustrated shows the short cannula branch 15 receiving the sliding obturator leg 34a while the long cannula branch 16 receives the relatively fixed obturator leg 34. However, this arrangement could be reversed if it is desired to initially start the longer branch 16 down the IVC. Such motion could be accompanied by tilting the obturator and cannula as shown in FIG. 22 to further assist placement of the long IVC branch 16.

Full retraction of the obturator following initial retraction of the sliding leg is facilitated with minimal frictional resistance due to the separate operation of the individual obturator legs in moving apart from the closed, gripping condition shown in FIG. 8 to the substantially open, release position shown in FIG. 9. Full retraction of the obturator from within the cannula results in full separation of the two cannula branches and their reception within the SVC and IVC as substantially shown in FIG. 14.

Removal of the cannula using the sliding leg obturator is accomplished in a manner similar to that described above.

Figure 24:
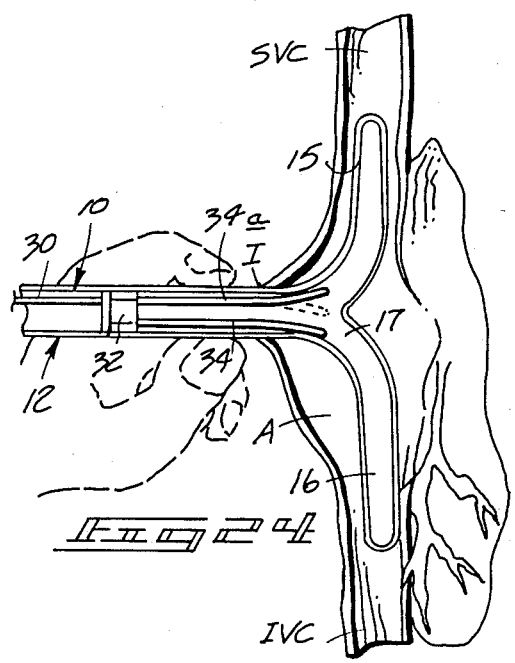

Operation of a double-curved rotatable release leg obturator and cannula combination is illustrated in FIGS. 22 through 24. With this arrangement, both obturator legs are bent or angled in a similar direction while one leg 34a is rotatable. The cannula and obturator may be angled on insertion as indicated at FIG. 22 to facilitate reception of the longer cannula branch 16 downwardly toward the IVC. This may be done to avoid accidental reception of the longer cannula branch 16 through the adjacent tricuspid valve (not shown).

Following initial insertion (FIG. 22), the obturator rod 30 may be rotated, along with the attached curved obturator leg 34a outwardly to the release position shown in FIG. 23. The curved leg 34a, rotated to this position, initiates the bend necessary for the short cannula branch 15 to follow when being directed upwardly for reception in the SVC. Following rotation, the obturator rod may be held stationary as the cannula is pushed on inwardly thereby allowing the IVC cannula branch 16 to diverge against the distal wall of the IVC, clearly avoiding the tricuspid valve. Next, the entire assembly may be tipped back to the position shown by FIG. 24. The surgeon may now continue to push the cannula inwardly to complete insertion. As this happens, the outwardly turned obturator legs influence divergence of the cannula branches until they are fully received within the SVC and IVC (FIG. 24). The surgeon may now rotate the rod 30 back, bringing the curved obturator leg 34a back to the closed position (shown by dashed lines in FIG. 24), at which time the obturator may be pulled axially from the cannula. Alternatively, the surgeon may gently pinch the cannula tube as shown in FIG. 24 adjacent the incision to assist inward springing of the curved obturator legs as the obturator is withdrawn.

Removal of the cannula using this version may be accomplished as discussed above with the possible exception that the rotatable leg 34a may be rotated to a neutral position (between gripping and open) to facilitate retraction of the cannula.

A combination of the steps indicated above for operation of the sliding leg obturator and the rotatable leg obturator are available with the release exemplified in FIG. 21, or in the double rod obturator arrangement illustrated in FIG. 10. Both of these versions, used separately or with variations including features of both, may be utilized to enable still further manipulative control of cannula branch separation within the atrium.

For example, a bend along the leg 34a may be rotated following insertion to initially move ends of the cannula apart to an initial, release orientation. Then the same leg 34a may be axially withdrawn to further facilitate motion of the adjacent cannula branch to its open, normal orientation. This movement could be followed by final retraction of the obturator from the cannula or by rotation and similar retraction of the remaining obturator leg when utilizing the double rod configuration shown in FIG. 10. Retraction of the cannula using either of the above obturators may involve steps similar to those used with the rotatable leg obturator described above. Of course, it is preferable that the cannula be retracted while both obturator legs are fully axially extended.

The several obturator configurations and cannula in the operations described above facilitate maximum manipulative capabilities within the atrium. Each form described includes features similar to the above versions, that facilitate low friction axial movement of the obturator within the cannula to selectively control divergence and convergence of the cannula branches.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. An improved venous drainage cannula assembly for insertion into the superior and inferior vena cavae through a single incision in the right atrium of the heart, comprising:

a tubular cannula member having a hollow tubular body with an interior central lumen defined by an interior wall surface, and a bifurcated tube end forming resilient tubular branches extending from a crotch section of the tubular body, each branch including a branch lumen opening into the central lumen;

wherein the resilient branches are normally oriented in diverging relaxed positions with respect to the tubular body to form a "T" configuration with the hollow tubular body;

an elongated obturator rod axially receivable within the cannula member;

a hub along the length of the obturator rod positioned thereon to be slidably received within the central lumen;

wherein the hub includes an annular wiping edge for slidably engaging the interior wall surface of the central lumen to prevent blood reflux through the control lumen upon insertion of the cannula branches into the atrium;

a pair of obturator legs projecting from the hub opposite the oburator rod for axially engaging the branches within the branch lumen, to selectively constrict the cannula branches together to facilitate insertion thereof through a single incision and for axial withdrawal relative to the cannula member to facilitate separation of the branches into their normal relaxed diverging positions, with one of the branches being received within the superior vena cava and the remaining branch being received in the inferior vena cava; and means on the obturator for minimizing frictional resistance to axial movement of the obturator rod and legs upon insertion of the obturator legs into the cannula branches and withdrawal of the obturator from the cannula.

2. The improved venous cannula assembly of claim 1 wherein the cannula branches include lumen of prescribed internal diameters and wherein the means for minimizing frictional resistance to axial movement of the obturator includes facing obturator leg surfaces adjacent ends of the legs for slidably engaging the branches along substantially tangential points of contact along the lumen thereof, and wherein the obturator legs include cross-sectional dimensions less than the internal diameters of the cannula branches.

3. The improved venous cannula assembly of claim 1 wherein the means for minimizing frictional resistance is further comprised of:

release means for enabling selective movement of one of the obturator legs relative to the other between a release position wherein the obturator legs are spaced apart by a first distance and a gripping position wherein at least portions of the obturator legs are spaced apart by a second distance less than the first distance.

4. The improved venous cannula assembly of claim 3 wherein the release means includes:

a bore formed through the hub means; and wherein one of the obturator legs is joined to the obturator rod and is received within the bore for selective axial movement within the bore independently of the other obturator leg to facilitate selective removal of the one obturator leg from an associated branch of the cannula independently of the other obturator leg.

5. The improved venous cannula assembly of claim 3 wherein the release means is comprised of:

a bore formed through the hub means; and wherein one of the obturator legs is joined to the obturator rod through the bore and is rotatable relative to the remaining obturator leg between the gripping position wherein the obturator legs are spaced close together relative one another so as to clamp the cannula branches securely together and the release position wherein the obturator legs are spaced apart from one another so as to unclamp the cannula branches and thereby facilitate separation of the cannula branches.

6. The improved venous cannula assembly of claim 1 wherein one of the resilient cannula branches includes a length dimension from the crotch section to a first open branch end greater than a length dimension along the remaining branch from the crotch section to a second branch end.

7. The improved venous cannula assembly of claim 1 wherein the means for minimizing frictional resistance is included within the obturator rod and legs wherein the cross-sectional dimensions of the obturator rod and legs are less than the respective cross-sectional dimensions across the central lumen and branch lumens such that the obturator legs are freely slidably received within the cannula branches and contact interior surfaces of the cannula branches along tangential points of contact.

8. The improved venous cannula assembly of claim 1 wherein at least one of the obturator legs includes a bend along the length thereof.

9. An improved venous drainage cannula assembly for insertion into the superior and inferior vena cavae through a single incision in the right atrium of the heart, comprising:

a tubular cannula member having a hollow tubular body with an interior central lumen, and a bifurcated tube end forming resilient tubular branches extending from a crotch section of the tubular body, each branch including a branch lumen opening into the central lumen;

wherein the resilient branches are normally oriented in diverging relaxed positions with respect to the tubular body to form a "T" configuration with the hollow tubular body;

an elongated obturator rod axially receivable within the cannula member;

a hub along the length of the obturator rod positioned thereon to be slidably received within the central lumen;

a pair of obturator legs projecting from the hub opposite the obturator rod for axially engaging the branches within the branch lumen, to selectively constrict the cannula branches together to facilitate insertion thereof through a single incision and for axial withdrawal relative to the cannula member to facilitate separation of the branches into their normal relaxed diverging configuration, with one of the branches being received within the superior vena cava and the remaining branch being received in the inferior vena cava; and means on the obturator for minimizing frictional resistance to axial movement of the obturator rod and legs upon insertion of the obturator legs into the cannula branches and withdrawal of the obturator from the cannula; and wherein the means for minimizing frictional resistance is comprised of release means for enabling selective movement of one of the obturator legs relative to the other between a release position wherein the obturator legs are spaced apart by a first distance and a gripping position wherein at least portions of the obturator legs are spaced apart by a second distance less than the first distance.

10. The improved venous cannula assembly of claim 9 wherein the release means includes:

a bore formed through the hub means; and wherein one of the obturator legs is joined to the obturator rod and is received within the bore for selective axial movement within the bore independently of the other obturator leg to facilitate selective removal of the one obturator leg from an associated branch of the cannula independently of the other obturator leg.

11. The improved venous cannula assembly of claim 9 wherein the release means is comprised of:

a bore formed through the hub means; and wherein one of the obturator legs is joined to the obturator rod through the bore and is rotatable relative to the remaining obturator leg between the gripping position wherein the obturator legs are spaced close together relative one another so as to clamp the cannula branches securely together and the release position wherein the obturator legs are spaced apart from one another so as to unclamp the cannula branches and thereby facilitate separation of the cannula branches.

12. An improved obturator for a bifurcated cannula having a hollow tubular body with a resilient bifurcated end formed by a pair of normally diverging resilient cannula branches, comprising:
   an elongated rod having a forward end adapted to be slidably received axially within the hollow tubular body of the bifurcated cannula;
   a hub along the rod;
   a pair of obturator legs extending axially from the hub opposite the elongated rod to remote obturator leg ends adapted to be slidably received within the cannula branches; and
   release means for selectively moving one of the obturator legs relative to the remaining obturator leg between a first position wherein the obturator leg ends are spaced closely together and are thereby adapted to clamp the cannula branches securely together for insertion through a single incision into the atrium, and a second position wherein the obturator leg ends are separated from one another to thereby enable separation of the cannula branches within the atrium and to facilitate retraction of the obturator from the cannula with minimal frictional resistance.

13. The improved obturator of claim 12 wherein the release means comprises a means mounting at least one of the obturator legs to the hub for longitudinal sliding movement, with respect to the remaining obturator leg between the first position wherein the obturator leg ends are longitudinally adjacent one another and the second position wherein the leg ends are spaced apart longitudinally from one another.

14. The improved obturator of claim 13 wherein the means mounting the one obturator leg is comprised of a bore formed within the hub receiving the one obturator leg for rotational movement therein about a longitudinal axis and wherein the end of the one leg is spaced laterally from the longitudinal axis.

15. The improved obturator of claim 12 wherein the release means comprises a means mounting one of the legs to the hub for rotational movement responsive to rotational movement of the rod about a longitudinal axis and wherein the end of the one leg is spaced laterally from the longitudinal axis.

16. The improved obturator of claim 12 further comprising an auxiliary rod extending substantially parallel to the elongated rod;
   wherein at least one of the obturator legs is connected to one of the rods and wherein the release means is comprised of the connected rod and leg movably received within a bore formed through the hub.

17. An improved obturator for a bifurcated cannula having a hollow tubular body defining a central lumen and with a resilient bifurcated end formed by a pair of normally diverging resilient cannula branches, each having a branch lumen opening into the central lumen;
   an elongated rod having a cross-sectional dimension less than the cross-sectional dimension of the central lumen such that the elongated rod may be freely slidably received axially within the central lumen;
   a hub along the length of the rod;
   a pair of obturator legs extending longitudinally from the hub, each having a cross-sectional dimension less than the cross-sectional dimensions of the branch lumen such that the legs are slidably received within the branch lumen and having facing surfaces thereon spaced transversely with respect to the length of the rod for slidably tangentially engaging walls of the branch lumens and camming the cannula branches together upon axial insertion of the obturator legs into the cannula branches and for permitting the cannula branches to resiliently separate upon withdrawal of the obturator legs axially with respect to the cannula branches;
   wherein the elongated rod and one of the obturator legs are integral; and
   wherein the hub includes a bore movably receiving the integral rod and the one obturator leg.

18. The improved obturator of claim 17 further comprising an auxiliary rod extending substantially parallel to the elongated rod and having a handle at one end and a remaining end connected to the hub.

19. The improved obturator of claim 17 wherein the integral rod and the one obturator leg are rotatable within the hub bore and wherein the one obturator leg includes a bent section along the length thereof such that rotation of the one obturator rod in the hub will cause corresponding rotation of the bent section toward and away from the remaining obturator leg.

20. The improved obturator of claim 19 wherein the integral rod and the one obturator leg are axially slidable within the hub in relation to the remaining obturator leg.

21. The improved obturator of claim 17 wherein the integral rod and the one obturator leg are axially slidable within the hub bore in relation to the remaining obturator leg.

22. The improved obturator of claim 21 further comprising stop means along the integral rod and the one obturator leg for selectively abutting the hub to limit axial movement of the one obturator leg relative to the remaining obturator leg.

* * * * *